United States Patent
Wik et al.

(10) Patent No.: US 9,770,171 B2
(45) Date of Patent: Sep. 26, 2017

(54) SYSTEMS AND METHODS FOR TRANSFER OF ON-BODY MEDICAL DEVICES BETWEEN NETWORKS

(71) Applicant: General Electric Company, Schenectady, NY (US)

(72) Inventors: Steven William Wik, Niskayuna, NY (US); David Michael Davenport, Niskayuna, NY (US); SM Shajedul Hasan, Rexford, NY (US)

(73) Assignee: General Electric Company, Niskayuna, NY (US)

( * ) Notice: Subject to any disclaimer, the term of this patent is extended or adjusted under 35 U.S.C. 154(b) by 35 days.

(21) Appl. No.: 14/972,170

(22) Filed: Dec. 17, 2015

(65) Prior Publication Data
US 2017/0172415 A1    Jun. 22, 2017

(51) Int. Cl.
| | |
|---|---|
| G08C 19/22 | (2006.01) |
| H04Q 9/00 | (2006.01) |
| A61B 5/00 | (2006.01) |
| H04W 4/00 | (2009.01) |
| H04L 29/08 | (2006.01) |

(52) U.S. Cl.
CPC ............ *A61B 5/0024* (2013.01); *H04L 67/04* (2013.01); *H04L 67/12* (2013.01); *H04L 67/14* (2013.01); *H04W 4/008* (2013.01)

(58) Field of Classification Search
CPC .............................. A61B 5/0024; H04W 4/008
USPC ..................................................... 340/870.07
See application file for complete search history.

(56) References Cited

U.S. PATENT DOCUMENTS

| | | |
|---|---|---|
| 5,375,604 A | 12/1994 | Kelly et al. |
| 7,978,062 B2 | 7/2011 | Lalonde et al. |
| 8,325,031 B1 | 12/2012 | Rao et al. |
| 8,549,600 B2 | 10/2013 | Shedrinsky |
| 8,638,218 B2 | 1/2014 | Simon et al. |
| 8,704,656 B2 | 4/2014 | Abedi |

(Continued)

OTHER PUBLICATIONS

Chen et al., "Implementing and evaluating a wireless body sensor system for automated physiological data acquisition at home", International Journal of Computer Science and Information Technology, vol. 2, No. 3, pp. 24-38, Jun. 2010.

(Continued)

*Primary Examiner* — Tanmay Shah
(74) *Attorney, Agent, or Firm* — Pabitra K. Chakrabarti

(57) ABSTRACT

A system for managing transfer of data in a medical body area network (MBAN) is presented. The system includes one or more sensor units disposed on a patient and configured to acquire data from the patient. Moreover, the system includes one or more detachable wireless communication and battery units, where the one or more detachable wireless communication and battery units are detachably coupled to a corresponding sensor unit. In addition, the system includes a patient monitoring device in bi-directional wireless communication with the one or more detachable wireless communication and battery units and configured to receive sensor data and maintain network connectivity between the one or more wireless communication and battery units and the patient monitoring device based on an operating condition of at least one wireless communication and battery unit of the one or more wireless communication and battery units.

23 Claims, 7 Drawing Sheets

(56) References Cited

U.S. PATENT DOCUMENTS

| | | |
|---|---|---|
| 8,825,120 B2 | 9/2014 | Chebbo et al. |
| 2010/0094098 A1 | 4/2010 | Smith et al. |
| 2012/0003933 A1 | 1/2012 | Baker et al. |
| 2014/0095102 A1 | 4/2014 | Potyrailo et al. |
| 2014/0135593 A1 | 5/2014 | Jayalth et al. |
| 2015/0149201 A1 | 5/2015 | Starmer, Jr. et al. |
| 2015/0349917 A1* | 12/2015 | Skaaksrud ......... G06Q 10/0833 370/328 |
| 2015/0351632 A1 | 12/2015 | Fuchs |
| 2016/0161985 A1* | 6/2016 | Zhang .................... G06F 1/163 361/679.03 |

OTHER PUBLICATIONS

SM Shajedul Hasan et al.; "Wireless Network Transfer", Pending U.S. Appl. No. 14/954,154, filed Nov. 30, 2015; 23 Pages.

A PCT Search Report and Written Opinion issued in connection with corresponding PCT Application No. PCT/US2016/055746 dated Jan. 26, 2017.

* cited by examiner

SYSTEMS AND METHODS FOR TRANSFER OF ON-BODY MEDICAL DEVICES BETWEEN NETWORKS

BACKGROUND

Embodiments of the present specification relate generally to patient monitoring and more particularly to systems and methods for the network transfer of on-body medical devices between wireless networks.

As will be appreciated, the general health of a patient is typically determined at least in part based on measurement and interpretation of key physiological indicators such as blood oxygen ($SPO_2$), blood pressure, temperature, and the like. Accordingly, monitoring the key physiological indicators is an important aspect of patient care. Such physiological indicators or data, however, are only of use if the indicators are transmitted in a timely and accurate manner.

Wireless sensor networks are widely used in the context of patient health monitoring. In particular, use of wireless sensor networks aids in circumventing problems associated with cable clutter and device management. In addition, the wireless transfer of data from patient sensors to a data display/patient monitoring device allows for the easier management of such a device and amelioration of burdens associated with cable management.

A wireless body area network (WBAN) includes wearable monitoring devices such as sensors which are often used to monitor a patient's vital signs (for example, blood pressure, heart rate, $SPO_2$, and the like) in a hospital's telemetry ward. The sensors used to monitor a patient's vital signs typically include a monitoring unit, a communication unit, and a power supply or battery unit. The sensors are controlled by a central controller device, which may also be referred to as a patient monitoring device, a communications Hub, or a controller Hub. Moreover, the critical nature of the information transmitted by a patient's WBAN may necessitate a very high transmission success rate, for example, about 95% and above. In some examples, a WBAN may be known as a medical body area network (MBAN). Specifically, an MBAN is a low power network of sensors worn on the body of the patient controlled by a hub device that is located either on the body or in close proximity to the body of the patient. The MBAN devices typically operate on a secondary basis in the 2360-2400 MHz band to prevent harmful interference from federal and non-federal stations operating in the band. MBAN devices support wireless non-voice data communications between body-worn medical sensor (client) devices and a dedicated programmer/control (P/C) device or patient monitoring device or Hub.

In order to satisfy the stringent requirements of data latency and outage in a WBAN/MBAN, it is desirable that the sensors remain operatively coupled to the patient and in communication with the patient monitoring device for the period during which the patient is monitored. Additionally, a power supply associated with the sensor, such as a battery unit, may discharge over time and cause the sensor to cease monitoring the patient and communicating patient data over the network, leading to the loss of critical physiological data. It is therefore desirable to monitor the power supply of the sensor and replace the power supply in a timely manner. However, absence of cables may result in lack of visual cues that are indicative of loss of connectivity with the patient. Moreover, the absence of cables also makes it difficult for a caregiver to determine if the sensors have adequate power supply and are communicating patient information to the patient monitoring device.

BRIEF DESCRIPTION

In accordance with aspects of the present specification, a system for managing transfer of data in a medical body area network (MBAN) is presented. The system includes one or more sensor units disposed on a patient and configured to acquire data from the patient. Moreover, the system includes one or more detachable wireless communication and battery units, where the one or more detachable wireless communication and battery units are detachably coupled to a corresponding sensor unit. In addition, the system includes a patient monitoring device in bi-directional wireless communication with the one or more detachable wireless communication and battery units and configured to receive sensor data and maintain network connectivity between the one or more wireless communication and battery units and the patient monitoring device based on an operating condition of at least one wireless communication and battery unit of the one or more wireless communication and battery units.

In accordance with another aspect of the present specification, a method for managing transfer of data in a medical body area network (MBAN) is presented. The method includes acquiring patient data via use of one or more sensor units disposed on a patient. Furthermore, the method includes transmitting the acquired sensor data via one or more wireless communication and battery units, wherein the one or more wireless communication and battery units are detachably coupled to a corresponding sensor unit. The method also includes pairing the one or more wireless communication and battery units with a patient monitoring device. In addition, the method includes maintaining network connectivity between the one or more wireless communication and battery units and the patient monitoring device based on an operating condition of at least one wireless communication and battery unit of the one or more wireless communication and battery units. A computer program product including a non-transitory computer readable medium, which in turn includes one or more tangible media, where the one or more tangible media include code adapted to perform the method is also presented.

DRAWINGS

These and other features and aspects of embodiments of the present specification will become better understood when the following detailed description is read with reference to the accompanying drawings in which like characters represent like parts throughout the drawings, wherein:

FIG. 1 is a schematic diagram of an exemplary system for wireless patient monitoring, in accordance with aspects of the present specification;

FIG. 2 is a flow chart illustrating a method for pairing a battery unit (WCBU) with a Hub (patient monitoring device) using proximity-based communication, in accordance with aspects of the present specification;

FIG. 3 is a flow chart illustrating another method for pairing a battery unit (WCBU) with a Hub using a user-entered code or pin, in accordance with aspects of the present specification;

FIG. 4 is a flow chart illustrating a method for associating a sensor with a WCBU via the Hub, in accordance with aspects of the present specification;

FIG. 5 is a flow chart illustrating a method for maintaining connectivity between the sensor and the Hub, in accordance with aspects of the present specification;

DETAILED DESCRIPTION

Figure 1:
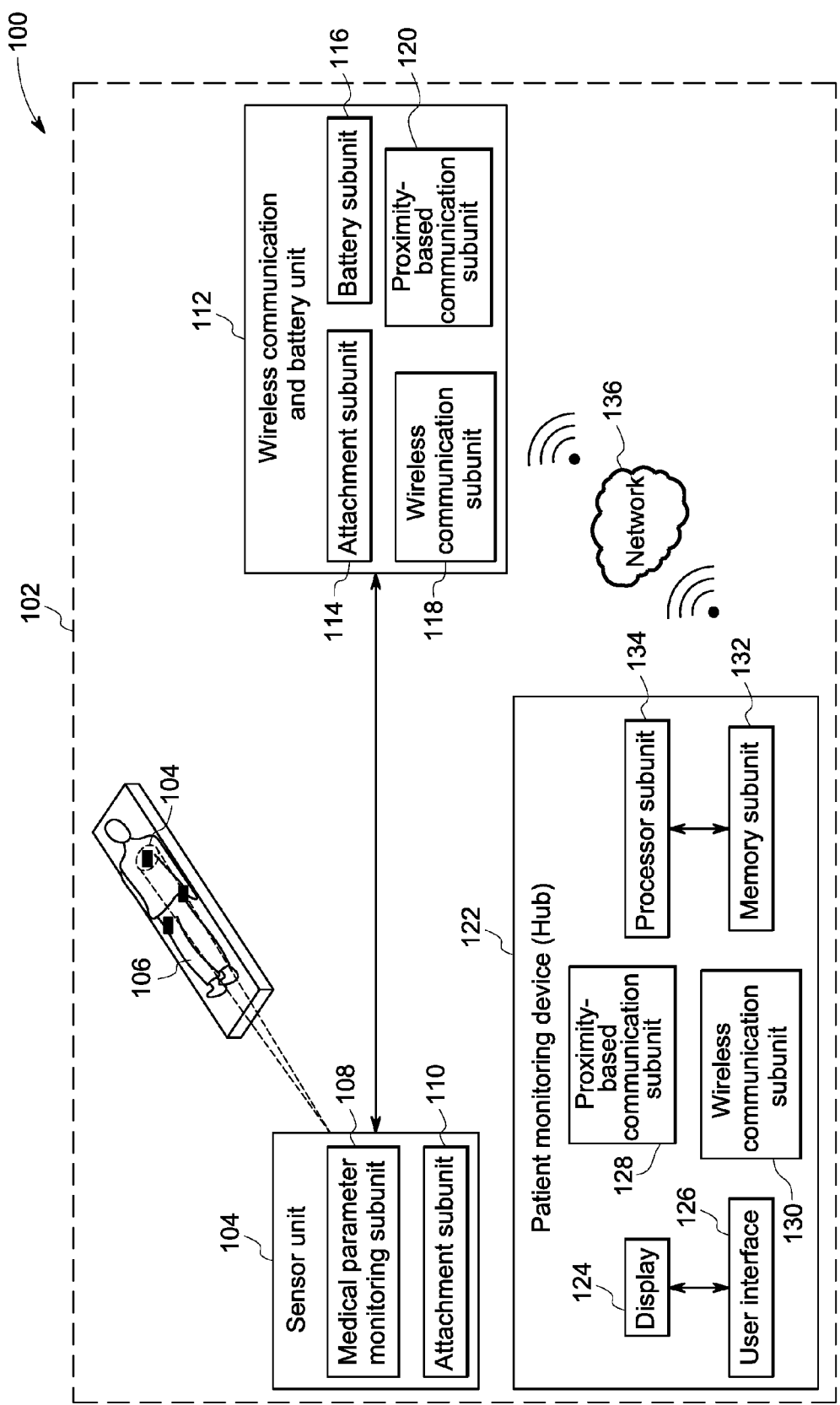

As will be described in detail hereinafter, various embodiments of exemplary systems and methods for wireless patient monitoring are presented. More particularly, the systems and methods presented herein aid in enhancing clinical workflow, network connectivity, and network transfer of on-body sensors in a patient monitoring system.

Although the following description includes embodiments relating to wireless patient monitoring in a hospital environment, these embodiments may also be implemented in other patient monitoring scenarios. For example, the embodiments of the present specification may be implemented for monitoring the patient in a clinic, at home, and/or in a mobile unit setting.

As used herein, the terms "processor" and "computer" and related terms, e.g., "processing device", "computing device", and "controller" are not limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Further, as used herein, the terms "software" and "firmware" are interchangeable, and include any computer program stored in memory for execution by personal computers, workstations, clients and servers.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

FIG. 1 illustrates an exemplary system 100 for wireless patient monitoring within a designated monitoring area 102. The designated monitoring area 102, for example, includes a hospital room that houses a patient 106 being monitored and/or one or more other regions within the hospital to which a patient 106 may move or be moved to, such as hospital corridors, elevator lobbies, patient lounges, cafeterias, laundry room, and/or kitchen. Alternatively, the designated monitoring area 102 may correspond to one or more regions within and/or outside a room in the patient's home, an assisted living facility, and/or a mobile medical unit.

In a presently contemplated configuration of FIG. 1, the system 100 includes one or more sensor units or sensor units 104 disposed on or about the patient 106. In addition, the system 100 also includes one or more wireless communication and battery units (WCBUs) 112 and a patient monitoring device (PMD) or Hub 122. It may be noted that for ease of illustration, the system is shown as including one sensor unit 104 and one wireless communication and battery unit (WBCU) 112. However, use of a plurality of sensor units 104 and a plurality of WBCUs 112 is envisioned. It may be noted that the terms PMD, patient monitoring device and Hub may be used interchangeably. Also, the terms sensor unit and sensor may be used interchangeably.

The sensor unit 104 may be operatively coupled to the WCBU 112 via respective attachment subunits. Each sensor unit 104 is operatively coupled to a corresponding WCBU. Moreover, the Hub 122 may be communicatively coupled to the WCBU 112 via a communications network 136. In one embodiment, the communications network 136 may be a wireless network. Also, the communications network 136, for example, may include a medical body area network (MBAN), a wireless body area network (WBAN), a wireless personal area network (WPAN), and/or any other suitable communications network.

In one embodiment, each sensor unit or sensor unit 104 includes a medical parameter monitoring subunit 114 and an attachment subunit 124. The medical parameter monitoring subunit 108 may be configured to sense and/or measure physiological parameters such as, but not limited to, $SPO_2$, blood pressure, and temperature. Also, the attachment subunit 110 of the sensor unit 104 may be used to detachably couple the sensor unit 104 to the WCBU 112. The WCBU 112 and the Hub 122 may be equipped to communicate using proximity-based communication technology, including, but not limited to, Near Field Communication (NFC), passive/active RFID (Radio Frequency Identification), optical, IR (Infra-Red) or magnetic pairing technology or point to point wireless techniques, including, but not limited to, WiFi, Bluetooth, Zigbee or other communication protocols.

More particularly, the detachable WCBU 112 and the Hub 122 may be equipped to communicate using proximity-based communication. The WCBU 112 and Hub 122 may be equipped with proximity-based communication subunits 120 and 128 respectively. The proximity-based communication subunits 120 and 128 may communicate via a proximity-based communication interface. Some non-limiting examples of proximity-based communication interfaces include NFC and RFID. Near Field Communication (NFC) enables devices capable of wireless communication to establish radio communication with each other by positioning the communicating devices in close proximity to one another. In one example, the desired distance separating the communicating devices is typically 10 cm (3.9 in) or less. Radio-Frequency Identification (RFID) is the wireless use of electromagnetic fields to transfer data. In other non-limiting examples, the proximity-based communication interface may include a magnetic field interface, an electric field interface, an optical interface, acoustic vibrations, ultrasound vibrations, mechanical vibrations, or combinations thereof.

Furthermore, in one embodiment, each WCBU 112 includes a wireless communications subunit 118, a battery subunit 116, and an attachment subunit 114. Additionally, in certain embodiments, the WCBU 112 may also include a proximity-based communication subunit 120. The wireless communication subunit 118 is configured to facilitate bi-directional wireless communication over the communications network 136. Moreover, the attachment subunit 114 is configured to facilitate detachably coupling the sensor unit 104 to the WCBU 112. Moreover, the proximity-based communication subunit 120 may be communicatively coupled with another proximity-based communication enabled device using the proximity-based communication protocol.

The communications network 136 is active within the designated monitoring area 102. Also, as previously noted, the communications network 136, for example, may include a wireless body area network (WBAN) or medical body area network (MBAN), a wireless personal area network (WPAN), and/or any other suitable communications network. It may be noted that the terms communications network and wireless network may be used interchangeably.

Moreover, in one embodiment, the Hub 122 may include a display 124, a user interface 126, a wireless communication subunit 130, and a proximity-based communication subunit 128. The proximity-based communication subunit 128 may be employed to communicatively couple the Hub 122 with another proximity-based communication enabled device using the same proximity-based protocol. In one example, the proximity-based communication subunits in the Hub 122 and the WCBU 112 may be NFC readers. Furthermore, the Hub 122 may also include a memory subunit 132 and a processor subunit 134. The wireless communication subunit 130 is configured to provide communication over the wireless network 136. Also, the memory subunit 132 is configured to store data generated by the sensor units 104. Also, the data generated by the sensor unit 104 may be communicated to the WCBU 112. The WCBU 112 in turn may communicate the sensor data to the wireless communication subunit 130 of the Hub 122. The processor subunit 134 of the Hub 122 may retrieve the sensor data from the wireless communication subunit 130 and store the data in the memory subunit 132. In certain embodiments, the processor subunit 134 may also be configured to create sensor unit and WCBU identification association lists, which in turn are stored by the processor subunit 132 in the memory subunit 134.

The messages between the Hub 122 and the WCBU 112 are transmitted and received over assigned communication channels at pre-determined frequencies. In one non-limiting example, the communication channels may use Time Division Multiple Access (TDMA) as a channel access method. The messages may include a payload component and a control component. In one embodiment, the payload component includes data and/or instructions and the control component includes control and/or timing information. Communication between the WCBU 112 and the Hub 122 is initiated by various pairing processes, which include the assignment by the Hub 122 of uplink/downlink TDMA time slots to the WCBU 112.

In some embodiments, the sensor units 104 may be wearable devices that are physically disposed on a desired region of the patient 106 for monitoring medically relevant information. Alternatively, in some embodiments, the sensor units 104 may include non-contact sensing devices, such as optical sensors that are configured to monitor the patient. Moreover, the sensor units 104 may be configured to measure one or more physiological indicators of the patient 106 continuously, at random points of time, after designated intervals of time, or combinations thereof.

Further, some examples of the sensor units 104 may include electrical surface potential sensors, bio-impedance sensors, accelerometer-based motion detectors, capacitive sensors, optical sensors, RF sensors, passive IR (PIR) sensors, and/or other suitable sensors. These sensor units 104 may be configured to monitor physiological indicators such as heartbeat, respiration, blood pressure, $SPO_2$, limb motion, and the like. Additionally, the sensor units 104 may measure other medically relevant information, for example, a level of a desired biological material such as hormones and/or non-biological material such as a contrast agent in the patient's body. The measured physiological parameters are transmitted to the patient monitoring device or Hub 122 via the WBCU 112 that is attached to a sensor unit 104.

In accordance with aspects of the present specification, through a combination of secure proximity-based and wireless pairing and a customized protocol, the system 100 allows the WCBUs 112 to be used universally with all medical sensor units. Additionally, proximity-based pairing allows medical personnel to easily pair the WCBUs 112 to a patient monitoring device or telemetry Hub 122. The pairing is made secure using an automatic encryption key generation and transfer. The WCBUs 112 are then coupled to the sensor units 104 disposed on the patient 106. The sensor units 104 acquire patient data and transmit the data to the Hub 122. The working of the system 100 will be described in greater detail with reference to FIGS. 2-8.

As noted hereinabove, the WBCU 112 may be paired with the Hub 122. In one embodiment, the WBCU 112 may be paired with the Hub 122 using proximity-based pairing. To that end, in one embodiment, the WBCU 112 may be positioned within a requisite distance of the Hub 122. In one example, a caregiver may position the WCBU 112 within the requisite distance from the Hub 122. The requisite distance may be representative of a proximity requirement set forth by the proximity-based pairing protocol. One example of a proximity-based pairing of the WBCU 112 with the Hub 112 is presented in FIG. 2.

Figure 2:
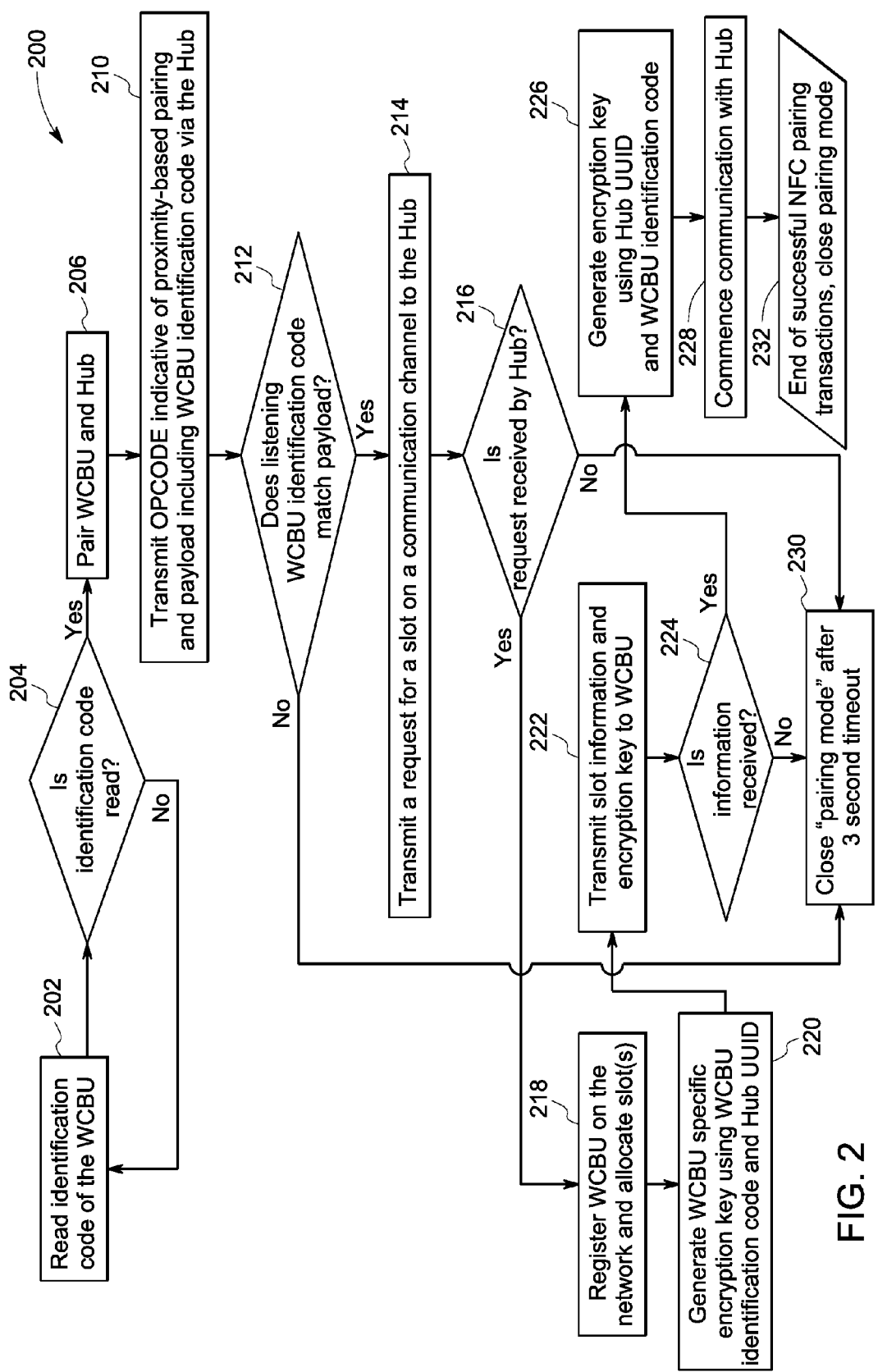

Referring now to FIG. 2, a flowchart 200 depicting a method for proximity-based pairing of a WBCU with a Hub is presented. The method 200 of FIG. 2 is described with reference to the elements of FIG. 1. In some embodiments, various steps of the method 200 of FIG. 2, more particularly, steps 202 through 228 may be performed by one or more of the processor subunit 134, the proximity-based communication subunits 120, 128, and the wireless communication subunits 118, 130.

Once the WCBU 112 is positioned within the requisite distance from the Hub 122, the Hub 122 reads the unique identification of the WCBU 112. In one example the unique identification may be the 7-byte Universally Unique Identifier (UUID) of the WCBU 112, as indicated by step 202. Furthermore, at step 204, a check is carried out to verify if the UUID read by the Hub 122 at step 202 matches the UUID of the WCBU 112. Accordingly, at step 204, if it is determined that the UUID read by the Hub 122 does not match the UUID of the WCBU 112, then control is passed back to step 202. However, at step 204, if it is determined that the UUID read by the Hub 122 matches the UUID of the WCBU 112, then control is passed to step 206.

Subsequently, at step 206, both the WCBU 112 and the Hub 122 may be paired. In the paired mode, a message payload between the Hub 122 and the WCBU 112 pertains exclusively to the process of pairing for a determined period of time. In one example, the determined time period may be about 3 seconds. Accordingly, for the duration of the determined time period, the message payload may not include any other information.

Moreover, in this pairing mode, the Hub 122 transmits a message, as indicated by step 210. In one example, the message may include an OPCODE indicative of the kind of pairing, for example, "NFC PAIRING." Additionally, the message payload may include the 7-byte UUID of the WCBU 112. Also, for the duration of the pairing mode, the WCBU 112 is configured to "listen" for a transmission from the Hub 122.

Once the WCBU 112 receives the transmission from the Hub 122, the WCBU 112 determines if the 7-byte UUID in the payload of the transmission from the Hub 122 matches a corresponding UUID. Accordingly, at step 212, a check may be carried out to determine if there is a match between the received UUID and the UUID of the WCBU 112. At step 212, if there is no match, the WCBU 112 continues in the listening mode until the duration of the pairing mode (for example, a timeout period) comes to an end. In one example, a timeout period is about 3 seconds. Subsequently, the WCBU 112 and the Hub 122 end the pairing mode after an unsuccessful attempt at proximity-based pairing, as depicted by step 230.

Referring again to step 212, if there is a match between the UUID in the payload of the transmission from the Hub 122 and the WCBU 112 UUID, then as indicated by step 214, the WCBU 112 transmits a request to the Hub 122 requesting a slot on the communication channel. As previously noted, these slots may be uplink/downlink TDMA time slots. Moreover, at step 216, a check is carried out to verify if the Hub 122 has received the request from the WCBU 112. At step 216, if the Hub 122 has not received the request from the WCBU 112, control is transferred to step 230, where the pairing mode is closed. However, at step 216, if it is verified that the Hub 122 received the request from the WCBU 112, the Hub 122 registers the WCBU 112 onto the wireless communication network 136, as depicted by step 218. Additionally, the Hub 122 allocates a communication slot to the WCBU 112.

Subsequently, at step 220, the Hub 122 generates a unique encryption key based on the 7-byte UUID of the WCBU 112 and the Hub's own UUID. Further, as indicated by step 222, the Hub 122 transmits a message to the WCBU 112 with the assigned slots as the payload. Also, at step 224, a check is carried out to verify if the WCBU 112 received the information from the Hub 122. At step 224, if it is verified that the WCBU 112 received the slot information, then, at step 226, the WCBU 112 generates the same encryption key as that generated by the Hub 122 at step 220, using the UUIDs of the WCBU 112 and the Hub 122. Moreover, as indicated by step 228, the WCBU 112 may commence data transmission including the encryption key in all subsequent messages to the Hub 122. Subsequently, the proximity-based pairing transactions may be successfully terminated and the pairing mode may be closed, as indicated by step 232. A successful termination of the process of FIG. 2 creates an operating state wherein the WCBU 112 and the Hub 122 are now "paired" and messages between the Hub 122 and the WCBU 112 may be transmitted over assigned communication slots using the specific encryption key created in steps 220 and 226.

Figure 3:
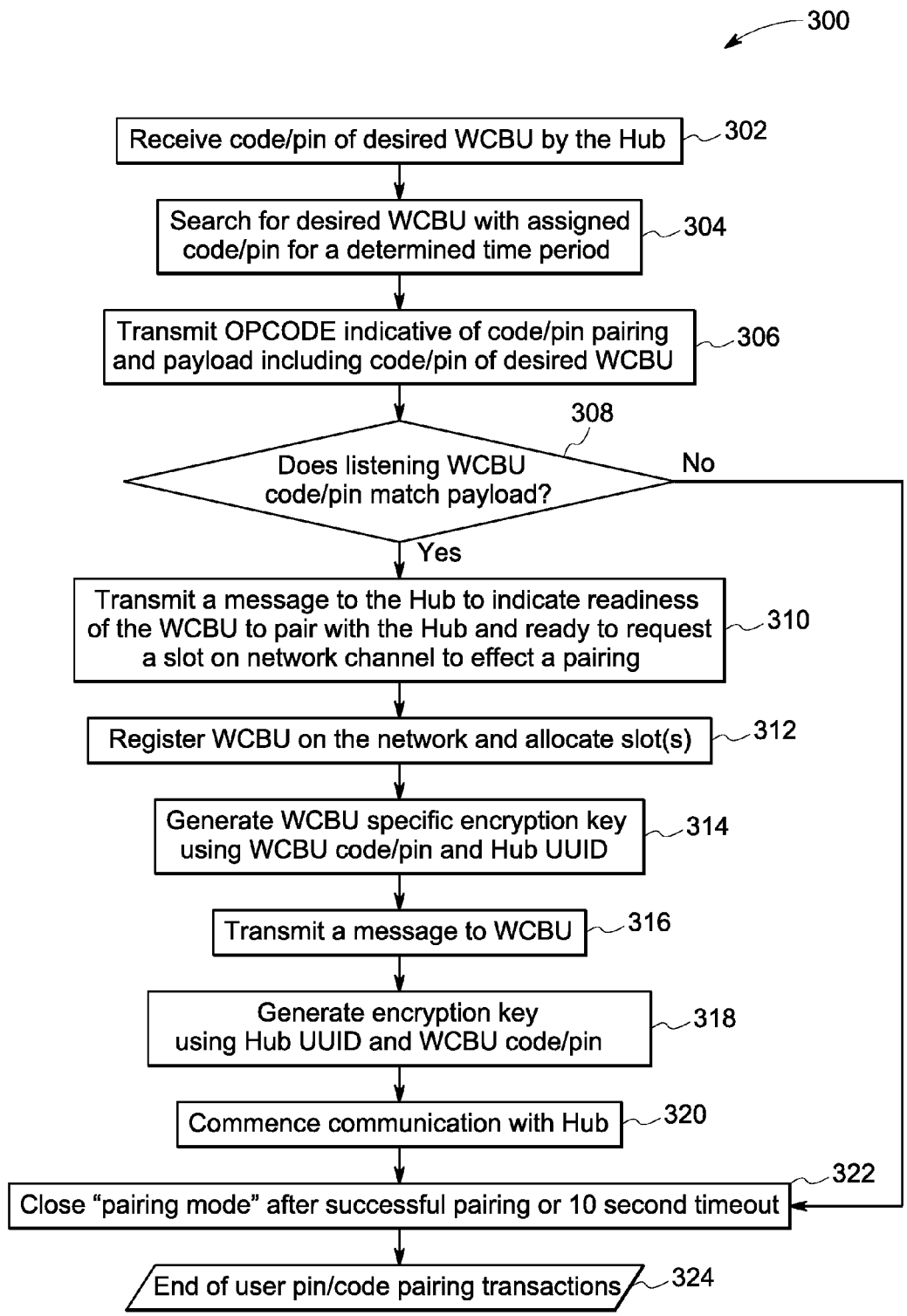

FIG. 3 is a flow chart illustrating another method 300 for pairing a battery unit (WCBU) with a Hub (patient monitoring device). In the method of FIG. 3, the unique identification of the WCBU to be paired with the Hub may be a user provided code or pin. The method 300 may be described with reference to the components of FIG. 1. In the present example, the WCBU 112 and the Hub 122 may be paired using a user pin/code pairing. In some embodiments, various steps of the method 300 of FIG. 3, more particularly, steps 302 through 324 may be performed by one or more of the processor subunit 134, the user interface 126, and the wireless communication subunits 118, 130. At step 302, the Hub 122 may receive a user pin/code. In one example, a user/caregiver may enter a code or pin using a user interface in the Hub 122 such as the user interface 126. The code or pin entered by the user may correspond to a desired WCBU 112.

Subsequent to receiving the user pin/code, at step 304, the Hub 122 initiates a determined time period for the user code/pin pairing. More particularly, the Hub 122 "searches" for a WCBU 112 corresponding to the user pin/code entered by the user for the duration of the determined time period. In one example, the determined time period may be about ten seconds.

Furthermore, at step 306, the Hub 122 broadcasts/transmits the user pin/code of the desired WCBU 112. In one example, the user pine/code may be transmitted via use of an OPCODE that is indicative of the pairing mode and a payload that includes the user pin/code of the desired WCBU 112. Once example of such an OPCODE is "code pairing." Subsequently, at step 308, a WCBU 112, which is listening for a transmission from the Hub 122, receives the transmission from the Hub 122. Additionally, at step 308, the listening WCBU 112 determines if the user pin/code in the payload of the received transmission matches its own user pin/code. If there is no match, control is passed on to step 322. At step 322, the WCBU 112 continues to listen for a broadcast from the Hub 122 for the duration of the determined time period of the pairing. When the determined time period (timeout period) expires, the Hub 122 stops broadcasting the message with the OPCODE "code pairing" and the payload including the user pin/code entered by the user, ending with an unsuccessful attempt at user pin/code pairing of the WCBU 112 with the Hub 122, as depicted by step 322. Reference numeral 324 depicts the end of the user pin/code pairing transactions.

With returning reference to step 308, if there is a match between the user pin/code in the payload of the message broadcasted from the Hub 122 and the WCBU 112 user pin/code, the WCBU 112 transmits a message to the Hub 122 indicating its readiness to pair with the Hub 122, as depicted by step 310. Additionally, the WCBU 112 also requests a communication channel slot and slot ID to effect a pairing with the Hub 122.

Subsequently, at step 312, the Hub 122 receives this transmission from the WCBU 112 and registers the WCBU 112 onto the wireless communication network 136. Also, the Hub 122 allocates a communication slot to the WCBU 112.

The allocated/assigned communication slot(s) may include uplink and downlink TDMA slots, in one example. Furthermore, at step 314, the Hub 122 generates a unique encryption key using the user pin/code of the WCBU 112 and its own UUID.

Moreover, at step 316, the Hub 122 transmits a message to the WCBU 112 with the assigned uplink and downlink TDMA slots. Also, at step 318, the WCBU 112 receives the slot information from the Hub 122 and generates the same encryption key as that generated by the Hub 122 at step 314, using the UUID of the Hub 122 and the user pin/code of the WCBU 112. The WCBU 112 may commence data transmission to the Hub 122 using the encryption key in all subsequent messages to the Hub 122, as indicated by step 320. Further, at step 322, the pairing mode between the Hub 122 and the WCBU 112 ends with a successful user pin/code pairing. Subsequently, the user pin/code pairing transactions may be terminated, as indicated by step 324.

Once the WCBU 112 and Hub 122 have achieved a successful pairing by any of the methods described with reference to FIGS. 2-3, it is desirable to physically couple the WCBU 112 to the sensor unit 104. Subsequent to the coupling of the WCBU 112 to the sensor unit 104, in accordance with aspects of the present specification, a UUID representative of the coupling of the sensor unit 104 with the corresponding WCBU 112 is generated and registered. In one example, the UUID of the sensor unit 104 is transmitted to the Hub 122. Subsequently, the processor subunit 134 associates the UUID of the sensor unit 104 with the WCBU 112 and registers/stores the association in memory.

Figure 4:
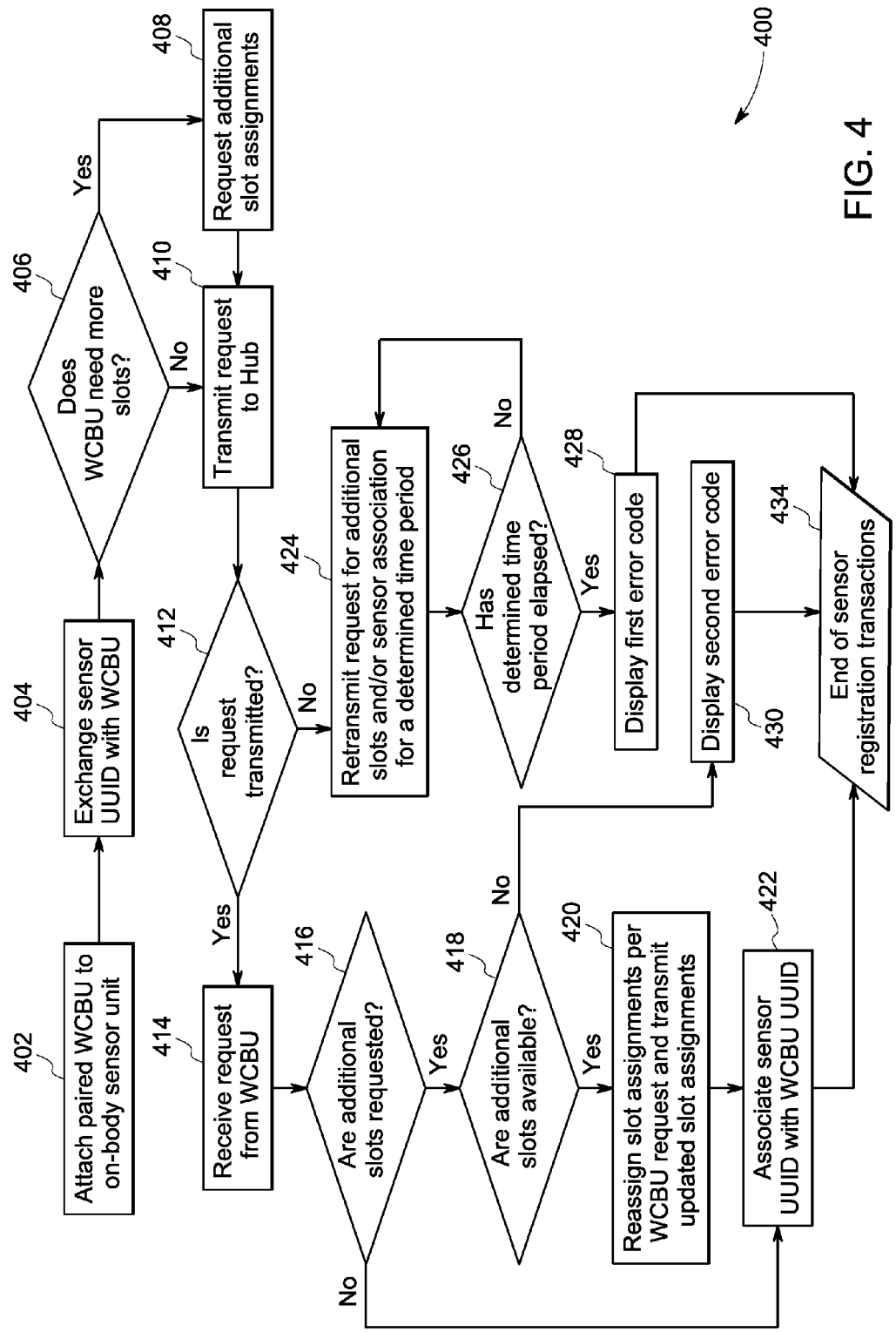

Referring now to FIG. 4, a flowchart 400 of a method of associating a sensor or sensor unit that is physically coupled to a WCBU with a Hub is presented. The method 400 is described with reference to the components of FIGS. 1-3. Also, it may be noted that the method 400 is described under the assumption that the WCBU 112 has been communicatively paired with the Hub 122 via use of proximity-based pairing (see FIG. 2) or user pin/code pairing (see FIG. 3). In some embodiments, various steps of the method 400 of FIG. 4, in particular, steps 402 through 430 may be performed by one or more of the processor subunit 134, the wireless communication subunits 118, 130, the display 124, and the memory unit 132.

At step 402, a user or caregiver physically couples or attaches a WCBU 112 to a sensor unit 104 disposed on or about the patient 106. In one example, the WCBU 112 may be physically coupled to the sensor unit 104 by physically linking the attachment subunit 124 of the sensor unit 104 to the attachment subunit 112 of the WCBU 112.

Further, at step 404, Universal Unique Identifier (UUID) information may be exchanged between the sensor unit 104 and the WCBU 112. In one example, the WCBU 112 retrieves the UUID of the sensor unit 104. Also, at step 406, the WCBU 112 assesses the need for additional communication slots. At step 406, if no additional communication slots are required, control is passed to step 410. However, if additional communication slots are required, then the WCBU 112 transmits a request for additional slot assignments to the Hub 122, as indicated by step 408. The WCBU 112 receives the UUID of the sensor unit 104 over a direct communication interface between the sensor unit 104 and WCBU 112, which may be serial, optical, infrared, or any other suitable direct communication interface. This link may be established when the two units are physically coupled together.

Moreover, at step 410 a request for associating the UUID of the sensor unit 104 with the UUID of the WCBU 112 is transmitted to the Hub 122. It may be noted that if the WCBU 112 has requested additional communication slots, then the request at step 410 may also include the slot assignment request of step 408.

In addition, a check may be carried out to verify if the request is transmitted successfully, as indicated by step 412. If the request transmission is successful, then at step 414, the Hub 122 receives the request from the WCBU 112. Furthermore, at step 416, the Hub 122 evaluates if additional communication slots have been requested. If no additional communication slots have been requested, control is passed to step 422, where the processor subunit 134 in the Hub 122 associates the UUID of the sensor unit 104 with the UUID of the WCBU 112. Also, processor subunit 134 may store this association in the memory subunit 150. However, at step 416, if the Hub 122 determines that additional communication slots have been requested, then the Hub 122 further determines if additional communication slots are available, as depicted by step 418. If additional slots are available, additional communication slots are allocated to the WCBU 112 and the updated communication slot assignments are transmitted to the WCBU 112, as indicated by step 420. Subsequently, at step 422, the processor subunit 134 associates the UUID of the sensor unit 104 with the UUID of the WCBU 112. Further, at step 434, the transaction of associating the sensor unit 104 with the WCBU 112 ends with a successful association.

Referring again to step 418, if the Hub 122 determines that additional communication slots are not available, control is passed to step 430, where a second error message is displayed. In one embodiment, the display subunit 110 of the Hub 122 may be employed to display the second error message. The second error message may be indicative of a failure to associate the sensor unit 104 with the WCBU 112 due to non-availability of additional slots. Also, in one example, the second error message may be visualized as "Insufficient Network Resources." Subsequently, at step 434, the transaction of associating the sensor unit 104 with the WCBU 112 may be terminated.

With returning reference to step 412, if the WCBU 112 fails to successfully transmit the request of step 410 to the Hub 122, the request for additional slots and/or associating the sensor unit 104 with the WCBU 112 may be retransmitted, as indicated by step 424. Also, the WCBU 112 continues to transmit the request for a determined time period (timeout period). In one example, the timeout period may be about 10 seconds. Further, at step 426, a check is carried out to verify if the determined time period or timeout period has elapsed. If the timeout period has elapsed, then a first error message indicative of a failure to associate the sensor unit 104 with the WCBU 112 due to the lapse of the timeout period may be displayed. In one embodiment, the display subunit 110 of the Hub 122 may be used to display the first error message. Also, in one example, the first error message may be visualized as "Time Out." Subsequently, at step 434, the transaction of associating the sensor unit 104 with the WCBU 112 may be terminated.

Additionally, the system protocol allows for seamless wireless network transfer of all sensors communicatively coupled to a patient monitoring device to other monitors/Hubs, thereby enabling medical personnel to efficiently use a cable-less system without the need for manual pairing and un-pairing for different patient scenarios.

Furthermore, if a patient is ambulatory and moves out of wireless communication range of the patient monitoring device, the system is designed to automatically reconnect the sensors disposed on the patient to the patient monitoring device/Hub without the intervention of the caregiver.

Subsequent to the successful association of the sensor UUID with the WCBU UUID by the Hub 122, the WCBU 112 retrieves patient data from the sensor unit 104 and transmits the data to the Hub 122 using the assigned communication slots. Over the course of time, the battery subunit 116 of the WCBU 112 may discharge and the power reserve of the WCBU 112 may be depleted. In the event of low power reserves of the battery subunit 116, a user or caregiver may detach the WCBU 112 having low power reserve or depleted power from the sensor unit 104 and physically couple a fresh WCBU 112 to the sensor unit 104.

In accordance with exemplary aspects of the present specification, a protocol that allows for battery swapping without the loss of network connectivity is provided. In particular, the protocol allows a sensor that is undergoing a change of a corresponding WCBU to continue to remain connected to a Hub during the swapping of the WCBU, thereby facilitating uninterrupted monitoring of the patient.

Figure 5:
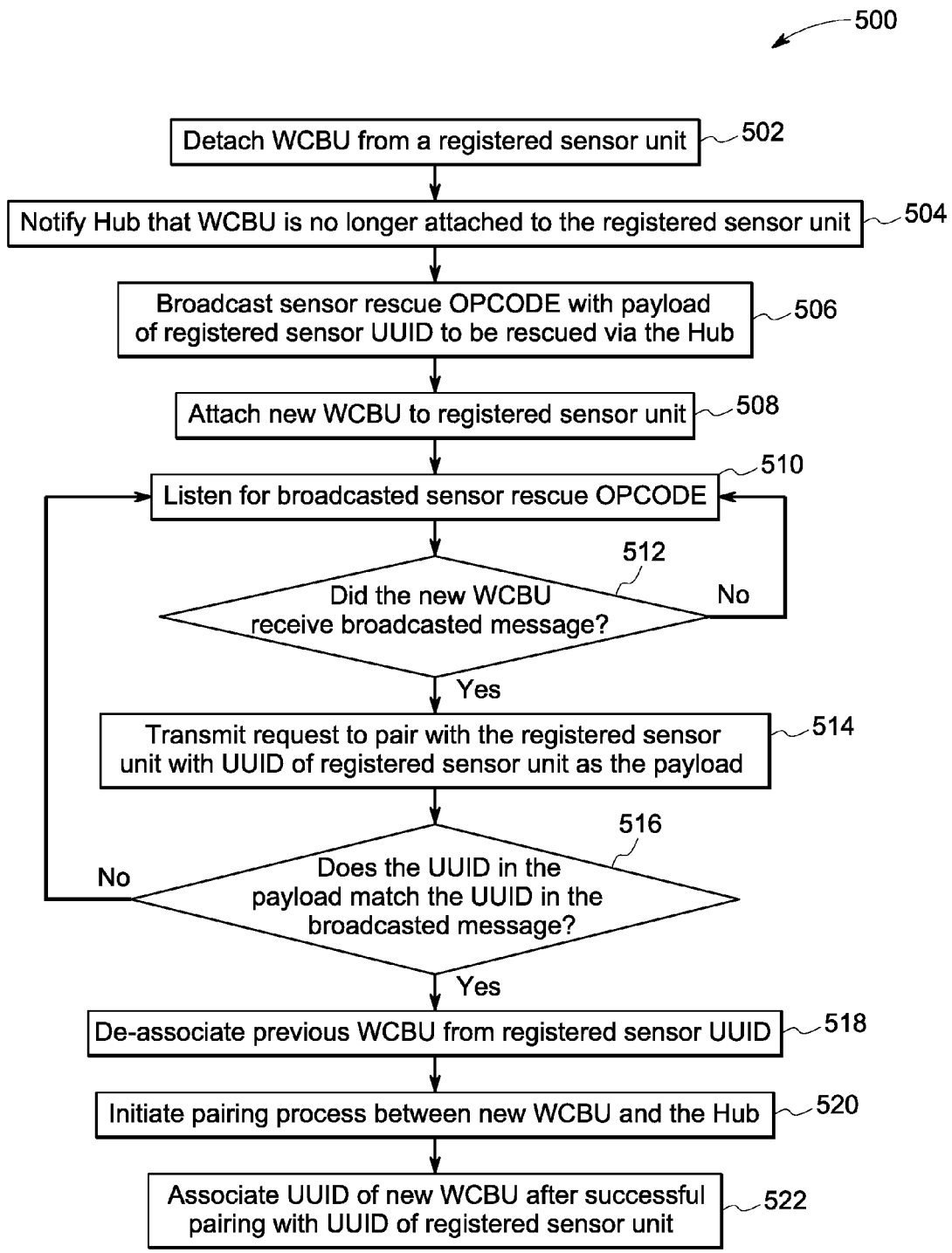

Detaching a WCBU from a sensor unit 104 may result in loss of connectivity with the Hub. The Hub is configured to maintain connectivity with the sensor. In particular, the Hub de-associates the depleted WCBU or the WCBU with the low power reserves from the sensor. Additionally, the Hub maintains the connectivity with the sensor while the corresponding WCBU is being replaced by broadcasting the UUID of the sensor for a determined time period until the fresh WCBU that is attached to the sensor responds and Hub associates the fresh WCBU with the sensor Turning now to FIG. 5, a flowchart 500 of a method for maintaining connectivity between a sensor and a patient monitoring device/Hub is presented. The method of FIG. 5 is described with reference to the components of FIGS. 1-4.

As previously noted, a WCBU 112 may be physically coupled to a sensor unit 104. Also, the UUID of the WCBU 112 may be associated with the UUID of the sensor unit 104 by the Hub 122. Also, it may be noted that the method 500 is described under the assumption that the WCBU 112 has been communicatively paired with the Hub 122 via use of proximity-based pairing (see FIG. 2) or user pin/code pairing (see FIG. 3).

Furthermore, it may be desirable to replace a depleted WCBU 112 or a WCBU 112 with low power reserve. Accordingly, in the method 500 of FIG. 5, at step 502, a user or caregiver may detach the WCBU 112 from the corresponding sensor unit 104. Hub. In one embodiment, the WCBU 112 may be detached from the sensor unit 104 by physically delinking the attachment subunit 124 of the sensor unit 104 from attachment subunit 114 of the WCBU 112.

Moreover, at step 504, the detached WCBU 112 transmits a message to the Hub 122 indicating that the WCBU 112 has been detached from the sensor unit 104. In addition, at step 506, the Hub 122 receives the transmission from the WCBU 112. In accordance with aspects of the present specification, the Hub 122 is configured to maintain connectivity with the sensor unit 104 associated with the WCBU 112 being replaced. In particular, the Hub 122 is configured to "rescue" the sensor unit 104 while the corresponding WCBU 112 is being replaced. Accordingly, the Hub 122 starts broadcasting a sensor rescue OPCODE. In one example, the sensor rescue OPCODE has a payload that includes the UUID of the sensor unit 104 to be rescued.

Also, at step 508, the user or caregiver attaches a second or new WCBU 112 to the sensor unit 104. The new WCBU 112 retrieves the sensor UUID from the sensor unit 104. In one example, the new WCBU 112 may be physically coupled to the sensor unit 104 by linking the attachment subunit 114 of second WCBU 112 to the attachment subunit 110 of the sensor unit 104. Subsequently, as indicated by step 510, the new WCBU 112 "listens" for the message (for example, the "sensor rescue" OPCODE) broadcast by the Hub 122. In one embodiment, the new WCBU 112 may be configured to "wake up" every second for about 200 ms over a period of about 1 minute to listen for the broadcasted message.

At step 512, a check may be carried out to verify if the new WCBU 112 received the message broadcasted by the Hub 122. If the new WCBU 112 receives the broadcasted message, then at step 514, the new WCBU 112 transmits a request to the Hub 122 to establish pairing with the sensor unit 104. The transmitted request may include the UUID of the sensor unit 104 as payload. However, if the new WCBU 112 does not receive the broadcasted message, then control may be passed back to step 510.

Furthermore, once the Hub 122 receives the request transmitted by the new WCBU 112, a check is carried out to verify if the UUID of the sensor unit 104 that is attached to the new WCBU 112 in the payload of the transmitted request matches with the UUID of the sensor unit broadcasted by the Hub 122 (see step 506), as indicated by step 516. If a match is detected, then at step 518, the Hub 122 de-associates the UUID of the previously detached WCBU 112 from the sensor unit 104 UUID in its memory subunit 132.

Subsequently, at step 520, the Hub 122 initiates a pairing process to pair with the new WCBU 112. In particular, the Hub 122 initiates the pairing process based on the UUID of the new WCBU 112 and an OPCODE. To that end, the Hub 122 transmits a request to pair with the new WCBU 112 using an OPCODE. One example of the OPCODE is "Sensor ID Pairing." The new WCBU 112 may be paired with the Hub 122 as previously described with reference to the method of FIG. 2, in one example. Once the new WCBU 112 and the Hub 122 are successfully paired, the Hub 122 and the processor subunit 134 in particular associates the UUID of the new WCBU 112 with the sensor unit 104 and registers/stores this association in the memory subunit 132, for example.

In certain scenarios, the patient 106 may be ambulatory and hence may move away from the designated patient monitoring area 102. In such situations, the WCBUs 112 connected to the on-body sensor units 104 may move out of range of the wireless network 136. In accordance with exemplary aspects of the present specification, the Hub 122 is configured to maintain connectivity with the on-body sensor units 104 disposed on the mobile patient 106. In particular, the processor subunit 134 of the Hub 122 maintains connectivity with the "out of range" on-body sensor units 104 by detecting an absence of transmission from the WCBUs 112 and subsequently initiating steps to reconnect.

Figure 6:
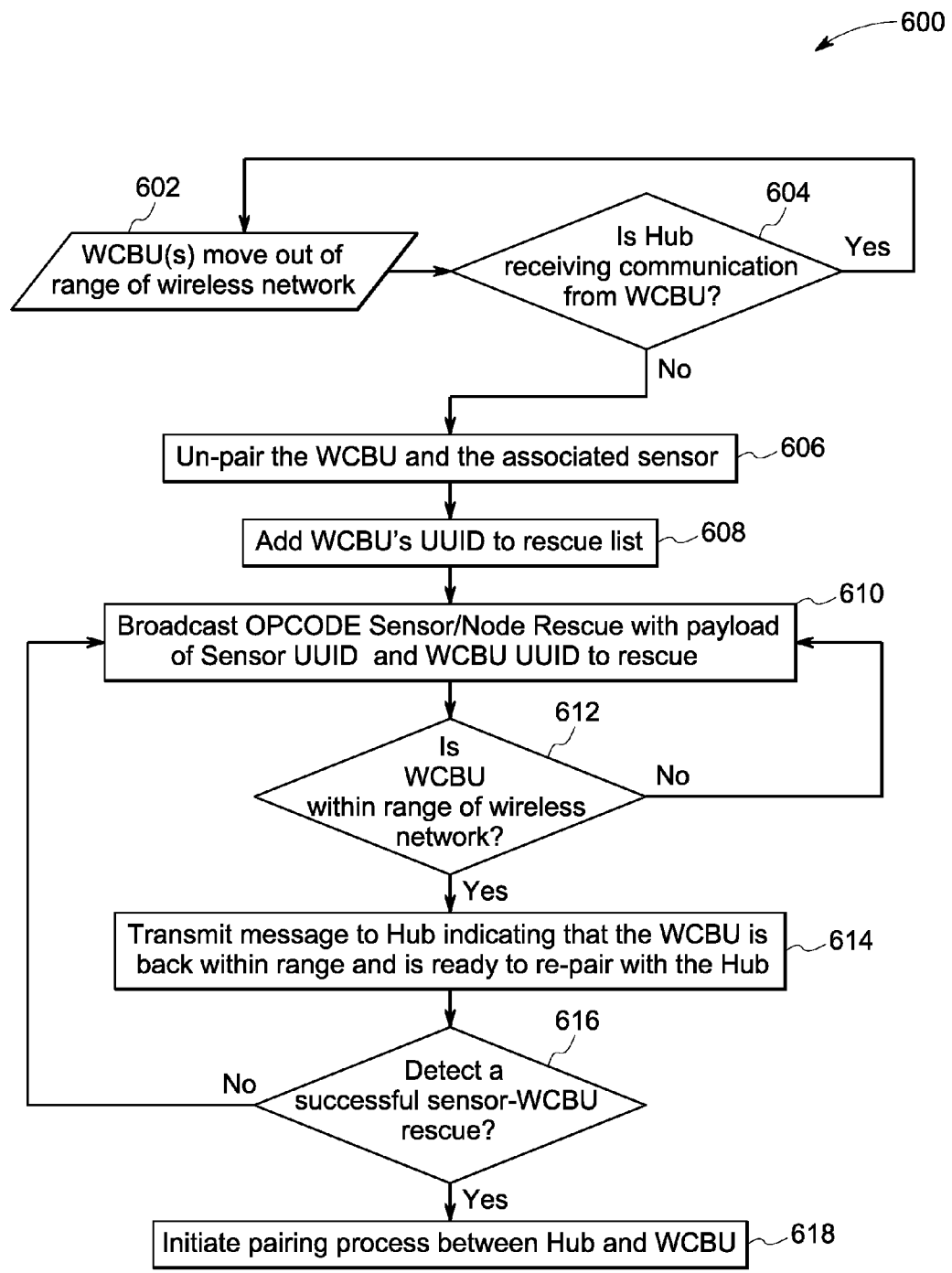
FIG. 6 is a flow chart illustrating a method for reconnecting a sensor and a corresponding WCBU of an ambulatory patient to the Hub, in accordance with aspects of the present specification.

Referring now to FIG. 6, a flowchart 600 of a method of reconnecting a sensor and WCBU pair disposed on a patient to a Hub is presented. The method 600 of FIG. 6 may be described with reference to the components of FIGS. 1-5. Also, it may be noted that the method 600 is described under the assumption that the WCBU 112 has been communicatively paired with the Hub 122 via use of proximity-based pairing (see FIG. 2) or user pin/code pairing (see FIG. 3).

As indicated by step 602, in certain situations, a patient 106 may move out of the designated patient monitoring area 102. Consequently, WCBUs 112 that are physically coupled to the on-body sensor units 104 move out of range of the wireless network 136, thereby impacting the communication between the WCBUs 112 and the Hub 122. Accordingly, at step 604, a check if carried out to verify if the Hub 122 is receiving any communication from the WCBU(s) 112. In one example, the Hub 122 may verify if the paired WCBUs 112 are transmitting over corresponding assigned communication slots. In one embodiment, the processor subunit 134 of the Hub 122 polls the wireless communication subunit 130 of the Hub 122 to verify if there is transmission from the paired WCBUs 112 over the corresponding assigned communication slots. At step 604, if it is verified that there is transmission from the paired WCBUs 112 over the corresponding assigned communication slots, control is returned to step 602. However, if the processor subunit 134 detects an absence of transmission from one or more of the paired WCBUs 112 associated with the sensor units 104, the processor subunit 134 internally un-pairs or de-associates the one or more WCBUs 112 from the corresponding sensor units 104, as indicated by step 606. In one example, the processor subunit 134 may retrieve the association lists from the memory subunit 132 and delete the WCBU UUID associated with the UUID of the corresponding sensor unit 104.

In addition, at step 608, the processor subunit 134 of the Hub 122 adds the UUIDs corresponding to the WCBUs 112 that are out of range to an internal rescue list. In one embodiment, this internal rescue list may be stored in the memory subunit 132. Furthermore, at step 610, the Hub 122 broadcasts a message via the wireless communication subunit 130 with an OPCODE "Sensor/Node Rescue" with a payload including the UUIDs of the sensor units 104 and the WCBUs 112 to be "rescued." In particular, the Hub 122 broadcasts the UUIDs of the WCBUs 112 in the internal rescue list and the UUIDs of the corresponding sensor units 104.

In certain scenarios, the patient 106 may move back into the designated monitoring area 102. Accordingly, the WCBUs 112 may also return to the range of wireless network 136. Hence, at step 612, a check may be carried out to verify if the WCBUs 112 are now within the range of the wireless network 136. If it is verified that the WCBUs 112 have returned to the range of the wireless network 136, the WCBUs 112 receive the message broadcasted from the Hub 122 (see step 610). Additionally, at step 614, the WCBUs 112 transmit a request to Hub 122 indicating the availability of the WCBUs 112 to communicatively re-pair with the Hub 122.

The Hub 122 may receive a transmission from one or more WCBUs 112. Accordingly, at step 616, the Hub 122 carries out a check to detect a successful sensor/node rescue. In particular, the Hub 122 checks for a sensor-WCBU pair rescue. At step 616, if a successful sensor-WCBU pair rescue is not detected, then control is transferred to step 610. However, at step 616, if a successful sensor-WCBU pair rescue is detected by the Hub 122, the Hub 122 may initiate a pairing process to communicatively re-pair with the WCBUs 112, as indicated by step 618. In one example, the Hub 122 may be communicatively re-paired with the WCBUs 122 using the method 200 of FIG. 2. Once all the WCBUs 112 coupled to the on-body sensor units 104 disposed on the patient 106 are successfully re-paired with the Hub 122, the process of re-pairing is terminated.

Figure 7:
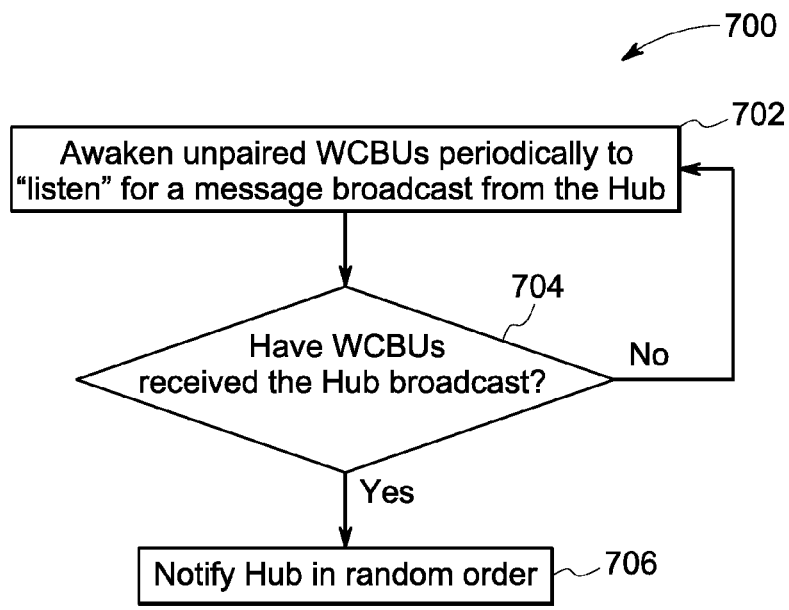
FIG. 7 is a flow chart illustrating a method for asset management of unpaired wireless communication and battery units (WCBUs), in accordance with aspects of the present specification.

In accordance with other aspects of the present specification, the Hub 122 may be configured to track all communicatively un-paired but live WCBUs 112 in the vicinity of the Hub 122. FIG. 7 is a flowchart 700 of a method for tracking one or more un-paired WCBUs 112 in the vicinity of the Hub 122. The method 700 is described with reference to the components of FIGS. 1-6.

At step 702, one or more unpaired WCBUs 112 may be configured to periodically listen for broadcast messages from the Hub 122 in the vicinity of the unpaired WCBUs 112. Furthermore, at step 704, a check may be carried out to verify if one or more of the unpaired WCBUs 112 have received the message broadcasted from the Hub 122. At step 704, if it is determined that the one or more unpaired WCBUs 112 did not receive the broadcasted message from the Hub 122, control may be passed back to step 702.

However, at step 704, if it is determined that one or more unpaired WCBUs 112 have received the message broadcasted from the Hub 122, then those unpaired WCBUs 112 Hub may notify the Hub 122 that the unpaired WCBUs 112 are currently located in the vicinity of the Hub 122, as indicated by step 706. In one example, the unpaired WCBUs 112 may notify the Hub 122 by transmitting a pinging message to the Hub 122. The pinging messages from the unpaired WCBUs 112 may be transmitted in a random order within a 3 second window, for example.

In certain situations, the sensor units 104 may be removed from the patient 106 when monitoring is no longer needed. In such a scenario, it may be desirable to communicatively unpair the WCBUs 112 that are operatively coupled to the detached sensor units 104 from the Hub 122.

Figure 8:
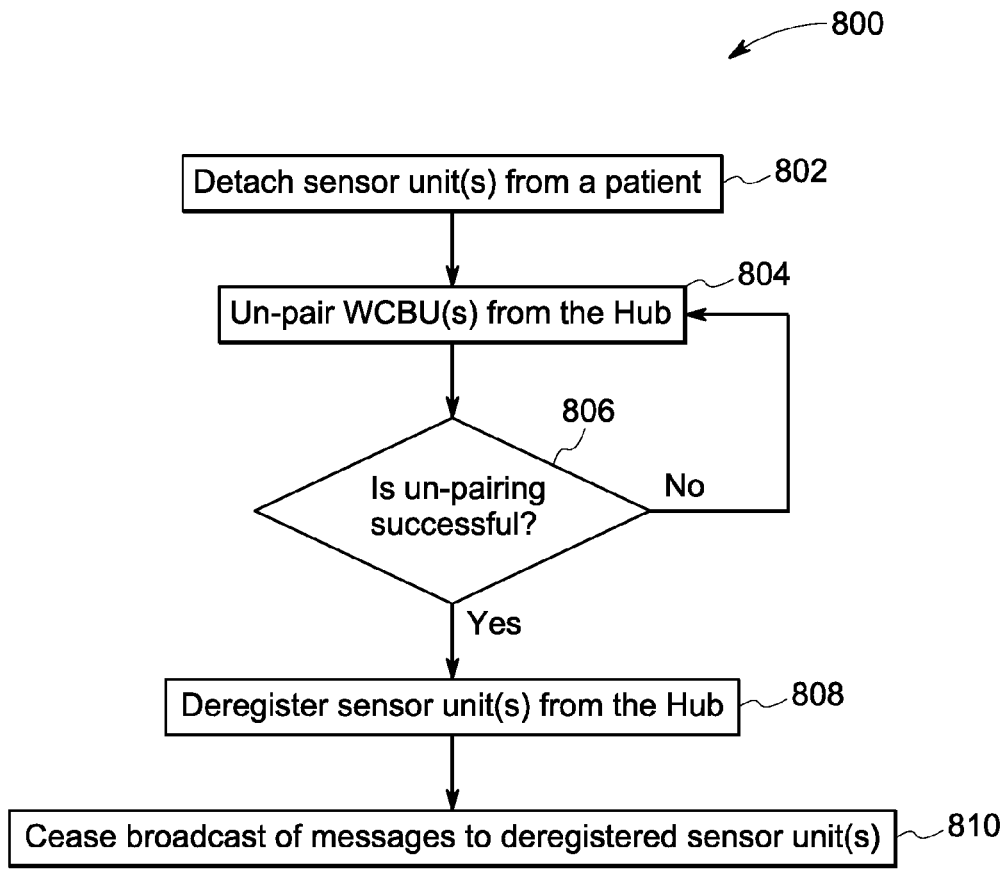
FIG. 8 is a flow chart illustrating a method for de-registering a sensor from the Hub, in accordance with aspects of the present specification.

FIG. 8 is a flowchart 800 depicting a method for communicatively un-pairing one or more WCBUs attached to sensors that have been removed from a patient. The method of FIG. 8 is described with reference to the components of FIGS. 1-7.

At step 802, one or more sensor units 104 may be detached from the patient 106. Subsequently, at step 804, WCBUs 112 corresponding to the detached sensor units 104 may be communicatively unpaired from the Hub 122.

Further, at step 806, a check may be carried out to verify if the unpairing is successful. If the un-pairing is successful, the UUIDs of the sensor units 104 that are associated with the unpaired WCBUs 112 may be deregistered. In one example, the processor subunit 134 in the Hub 122 may be configured to remove the UUIDs of the sensor units 104 corresponding to the unpaired WCBUs 112 from the association list maintained by the Hub 122 in the memory subunit 132. However, if the un-pairing is unsuccessful, control may be passed back to step 804. Moreover, at step 808, following the successful deregistration of the sensor units 104, the Hub 122 may be configured to cease broadcast of any messages to the deregistered sensor units 104.

The systems and methods for monitoring a patient presented hereinabove enhance clinical workflow for caregivers and/or other medical personnel in in-hospital and/or out-of-hospital settings. The on-body sensors in the system are in bi-directional communication with a patient monitoring device or Hub over a wireless communication network through a combination of secure proximity-based pairing and a customized protocol, thereby allowing the WCBUs to be used universally with all medical sensor units. Additionally, proximity-based pairing allows medical personnel to easily pair the WCBUs to a patient monitoring device or telemetry Hub via a secure, automatic proprietary encryption key generation and transfer. Additionally, the custom protocol allows for battery swapping without the loss of network connectivity when a sensor unit is undergoing a change of a battery unit by maintaining connectivity to the Hub. The systems and methods also provide for seamless wireless network transfer of all sensors communicatively coupled to the Hub to other monitors/Hubs, thereby enabling medical personnel to efficiently use a cable-less system while circumventing the need for manual pairing and unpairing for different patient scenarios. Furthermore, if a patient is ambulatory and moves out of wireless communication range of the patient monitoring device, the system is designed to automatically reconnect the sensors on the patient to the patient monitoring device without the intervention of the caregiver.

Additionally, the systems and methods described herein alert the patient monitoring device/Hub when sensor units are not communicating over the WBAN/MBAN, and initiate a reconnect protocol when such sensor units go out-of-range from the patient monitoring device. Furthermore, the patient monitoring device/Hub may be notified of low power reserve on a sensor unit power supply, thereby enabling timely replacement of the battery unit with no loss of network connectivity. Moreover, the systems and methods permit the transfer the sensor units associated with one patient monitoring device/Hub, as a group, to another such device with ambulatory capabilities, for example, when the patient is mobile.

It is to be understood that not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, it should be readily understood that the specification is not limited to such disclosed embodiments. Rather, the technology can be modified to incorporate any number of variations, alterations, substitutions or equivalent arrangements not heretofore described, but which are commensurate with the spirit and scope of the claims. Additionally, while various embodiments of the technology have been described, it is to be understood that aspects of the specification may include only some of the described embodiments. Accordingly, the specification is not to be seen as limited by the foregoing description, but is only limited by the scope of the appended claims.

The invention claimed is:

1. A system for managing transfer of data in a medical body area network (MBAN), the system comprising:
one or more sensor units disposed on a patient and configured to acquire data from the patient;
one or more detachable wireless communication and battery units, wherein the one or more detachable wireless communication and battery units are detachably coupled to a corresponding sensor unit;
a patient monitoring device in bi-directional wireless communication with the one or more detachable wireless communication and battery units and configured to:
receive sensor data;
maintain network connectivity between the one or more wireless communication and battery units and the patient monitoring device based on an operating condition of at least one wireless communication and battery unit of the one or more wireless communication and battery units, wherein to maintain the network connectivity, the patient monitoring device is configured to:
de-associate an unique identification of the at least one wireless communication and battery unit from a unique identification of the corresponding sensor unit based on the operating condition of the at least one wireless communication and battery unit; and
associate the unique identification of the sensor unit with a unique identification of a second of the one or more wireless and communication and battery units to detachably couple the second of the one or more wireless and communication and battery units to the sensor unit based on a request from the second of the one or more wireless and communication and battery units, wherein the second of the one or more wireless communication and battery units is detachably coupled to the sensor unit via an attachment subunit of the sensor unit and an attachment subunit of the second of the one or more wireless communication and battery units.

2. The system of claim 1, wherein the patient monitoring device comprises:
a proximity-based communication subunit configured to obtain the unique identification corresponding to the at least one wireless communication and battery unit using a proximity-based communication interface;
a wireless communication subunit configured to:
broadcast the unique identification of the at least one wireless communication and battery unit;
receive a request from the at least one wireless communication and battery unit having the unique identification; and
transmit information in response to the request to the at least one wireless communication and battery unit.

3. The system of claim 2, wherein the one or more wireless communication and battery units further comprise:
a proximity-based communication subunit configured to transmit and receive data using the proximity-based communication interface;
a wireless communication subunit configured to transmit and receive data over a wireless network;
a battery subunit configured to supply power to a corresponding sensor unit; and
an attachment subunit configured to detachably couple the wireless communication and battery unit to the corresponding sensor unit.

4. The system of claim 2, wherein the one or more sensor units comprise:
a medical parameter monitoring subunit configured to sense data from the patient; and
an attachment subunit configured to detachably couple the one or more sensor units to a corresponding wireless communication and battery unit.

5. The system of claim 2, wherein the proximity-based communication interface comprises a Near Field Communications interface, a Radio Frequency Identification interface, a magnetic field interface, an electric field interface, an optical interface, acoustic vibrations, ultrasound vibrations, mechanical vibrations, or combinations thereof.

6. The system of claim 2, wherein the unique identification comprises a unique identification code of the at least one wireless communication and battery unit.

7. The system of claim 2, wherein the wireless communication subunit of the wireless communication and battery unit is further configured to transmit the unique identification of the corresponding sensor unit to the patient monitoring device.

8. The system of claim 2, wherein the patient monitoring device further comprises:
a memory subunit configured to store data; and
a processor subunit configured to store an association of the unique identification of the one or more wireless communication and battery units with an unique identification of corresponding sensor unit in the memory subunit.

9. The system of claim 2, wherein the operating condition of the at least one wireless communication and battery unit comprises a detached state or an out of range state.

10. The system of claim 2, wherein the wireless communication subunit of the at least one wireless communication and battery unit is further configured to transmit the operating condition of the at least one wireless communication and battery unit to the patient monitoring device.

11. The system of claim 10, wherein the patient monitoring device is further configured to:
broadcast the unique identification of the corresponding sensor unit of the at least one wireless communication and battery unit.

12. The system of claim 10, wherein the wireless communication subunit of the second of the one or more wireless communication and battery units is further configured to:
receive the broadcast having the unique identification of the sensor unit from the patient monitoring device; and
transmit a request to the patient monitoring device to be associated with the sensor unit.

13. The system of claim 12, wherein the patient monitoring device is further configured to:
receive the request from the wireless communication and battery unit corresponding to the second of the one or more wireless and communication and battery units and the unique identification of the sensor unit.

14. The system of claim 10, wherein the wireless communication subunit of the patient monitoring device is further configured to broadcast the unique identification of the at least one wireless communication and battery unit and the unique identification of the corresponding sensor.

15. The system of claim 14, wherein the wireless communication subunit of the at least one wireless communication and battery unit is further configured to:
receive the broadcast signal from the patient monitoring device when the at least one wireless communication and battery unit is within communicative range of the patient monitoring device; and
transmit a request to re-pair with the patient monitoring device.

16. A method for managing transfer of data in a medical body area network (MBAN), the method comprising:
acquiring patient data via use of one or more sensor units disposed on a patient;
transmitting the acquired sensor data via one or more wireless communication and battery units, wherein the one or more wireless communication and battery units are detachably coupled to a corresponding sensor unit;
pairing the one or more wireless communication and battery units with a patient monitoring device, wherein the pairing comprises:
obtaining, by a patient monitoring device, a unique identification of at least one of the one or more wireless communication and battery units;
receiving, by the patient monitoring device, a request and the unique identification from the at least one wireless communication and battery unit;
obtaining, by the at least one wireless communication and battery unit, a unique identification of a sensor detachably coupled to the at least one wireless communication and battery unit;
associating the unique identification of the sensor with the unique identification of the at least one wireless communication and battery unit; and
maintaining network connectivity between the one or more wireless communication and battery units and the patient monitoring device based on an operating condition of at least one wireless communication and battery unit of the one or more wireless communication and battery units, wherein maintaining the network connectivity comprises:
transmitting, by the at least one wireless communication and battery unit, the operating condition to the patient monitoring device;
de-associating, by the patient monitoring device, the unique identification of the at least one wireless communication and battery unit from the unique identification of the corresponding sensor unit; and
associating, by the patient monitoring device, the unique identification of the sensor unit with a unique identification of the second wireless communication and battery unit.

17. The method of claim 16, wherein the pairing further comprises:
broadcasting, by the patient monitoring device, the unique identification of at least one wireless communication and battery unit;
and
transmitting, by the patient monitoring device, information in response to the request to the at least one wireless communication and battery unit.

18. The method of claim 16, wherein obtaining the unique identification comprises reading, by the patient monitoring device, a Universal Unique Identifier (UUID) from the at least one wireless communication and battery unit using a proximity based protocol, wherein the Universal Unique Identifier comprises a unique identification code of the at least one wireless communication and battery unit.

19. The method of claim 17, wherein the pairing further comprises:
transmitting the unique identification of the sensor to the patient monitoring device.

20. The method of claim 16, wherein maintaining the network connectivity further comprises:
de-associating, by the patient monitoring device, the unique identification of the sensor unit from the at least one wireless communication and battery unit; and
broadcasting, by the patient monitoring device, the unique identification of the sensor unit.

21. The method of claim 20, further comprising:
attaching the second wireless communication and battery unit of the one or more wireless communication and battery units to the sensor unit;
receiving, by the second wireless communication and battery unit, the broadcasted message from the patient monitoring device; and
transmitting, by the second wireless communication and battery unit, a request to the patient monitoring device to be associated with the sensor unit.

22. The method of claim 20, wherein maintaining the network connectivity comprises:
broadcasting, by the patient monitoring device, the unique identification of the at least one wireless communication and battery unit and the unique identification of the corresponding sensor unit;

receiving, by the at least one wireless communication and battery unit, the broadcast signal from the patient monitoring device when the at least one the wireless communication and battery unit is within communicative range of the patient monitoring device; and transmitting, by the at least one wireless communication and battery unit, a request to re-pair with the patient monitoring device.

23. A non-transitory computer readable medium that stores instructions executable by one or more processors to perform a method managing transfer of data in a medical body area network, comprising:

acquiring patient data via use of one or more sensor units disposed on a patient;

transmitting the acquired sensor data via one or more wireless communication and battery units, wherein the one or more wireless communication and battery units are detachably coupled to a corresponding sensor unit;

pairing the one or more wireless communication and battery units with a patient monitoring device, wherein the pairing comprises:

obtaining, by a patient monitoring device, a unique identification of at least one of the one or more wireless communication and battery units;

receiving, by the patient monitoring device, a request and the unique identification from the at least one wireless communication and battery unit;

obtaining, by the at least one wireless communication and battery unit, a unique identification of a sensor detachably coupled to the at least one wireless communication and battery unit;

associating the unique identification of the sensor with the unique identification of the at least one wireless communication and battery unit;

maintaining network connectivity between the one or more wireless communication and battery units and the patient monitoring device based on an operating condition of at least one wireless communication and battery unit of the one or more wireless communication and battery units, wherein maintaining the network connectivity comprises:

transmitting, by the at least one wireless communication and battery unit, the operating condition to the patient monitoring device;

de-associating, by the patient monitoring device, the unique identification of the at least one wireless communication and battery unit from the unique identification of the corresponding sensor unit; and associating, by the patient monitoring device, the unique identification of the sensor unit with a unique identification of the second wireless communication and battery unit.

* * * * *